(12) United States Patent
Lauritzen et al.

(10) Patent No.: US 9,302,107 B2
(45) Date of Patent: Apr. 5, 2016

(54) CORTICAL VISUAL PROSTHESIS

(71) Applicant: Second Sight Medical Products, Inc., San Fernando, CA (US)

(72) Inventors: Thomas Lauritzen, San Francisco, CA (US); Jessy D Dorn, Los Angeles, CA (US); Robert J Greenberg, Los Angeles, CA (US); Jordan Matthew Neysmith, Pasadena, CA (US); Neil Hamilton Talbot, La Crescenta, CA (US); David Daomin Zhou, Saugus, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

(21) Appl. No.: 14/172,785

(22) Filed: Feb. 4, 2014

(65) Prior Publication Data

US 2014/0222103 A1 Aug. 7, 2014

Related U.S. Application Data

(60) Provisional application No. 61/760,583, filed on Feb. 4, 2013.

(51) Int. Cl.
| *A61N 1/00* | (2006.01) |
| *A61N 1/36* | (2006.01) |
| *A61N 1/05* | (2006.01) |
| *A61N 1/375* | (2006.01) |
| *A61N 1/04* | (2006.01) |
| *A61N 1/372* | (2006.01) |

(52) U.S. Cl.
CPC .......... *A61N 1/36046* (2013.01); *A61N 1/0531* (2013.01); *A61N 1/0476* (2013.01); *A61N 1/375* (2013.01); *A61N 1/37205* (2013.01)

(58) Field of Classification Search
CPC .................................... A61N 1/36046
USPC .................................... 607/54, 152
See application file for complete search history.

(56) References Cited

U.S. PATENT DOCUMENTS

| 4,573,481 | A | 3/1986 | Bullara |
| 4,628,933 | A | 12/1986 | Michelson |
| 4,837,049 | A | 6/1989 | Byers et al. |
| 5,109,844 | A | 5/1992 | de Juan, Jr. et al. |
| 5,215,088 | A | 6/1993 | Normann et al. |
| 5,935,155 | A | 8/1999 | Humayun et al. |
| 6,400,989 | B1 | 6/2002 | Eckmiller |
| 6,458,157 | B1 | 10/2002 | Suaning |
| 2012/0296444 | A1* | 11/2012 | Greenberg et al. ............. 623/25 |
| 2012/0323288 | A1 | 12/2012 | Anderson et al. |

FOREIGN PATENT DOCUMENTS

| WO | WO2011067297 A1 | 6/2011 |
| WO | WO2012167096 A2 | 12/2012 |

* cited by examiner

*Primary Examiner* — Nicole F. Lavert
*Assistant Examiner* — Nadia A Mahmood
(74) *Attorney, Agent, or Firm* — Scott B. Dunbar

(57) ABSTRACT

The present invention is a visual prosthesis adapted for implantation in the brain, and more particularly with an electrode array adapted for implantation in the Calcarine Sulcus of the visual cortex. The electrode array of the invention has electrodes on each side and spaced appropriately for the Calcarine Sulcus and driven by an electronic circuit within a hermetic package small enough to be implanted with a skull.

16 Claims, 8 Drawing Sheets

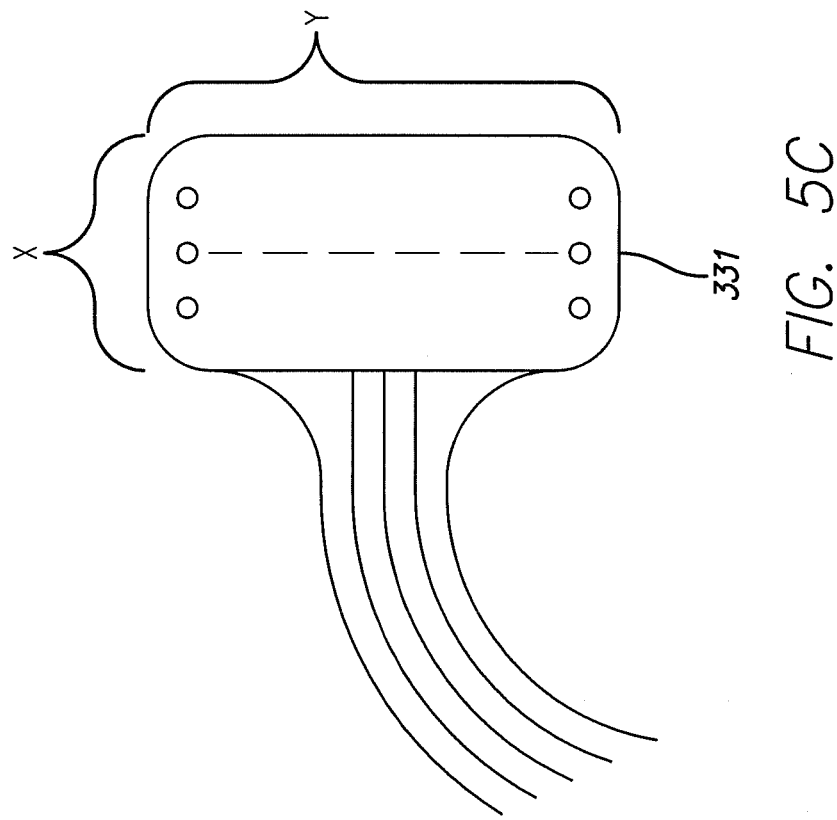
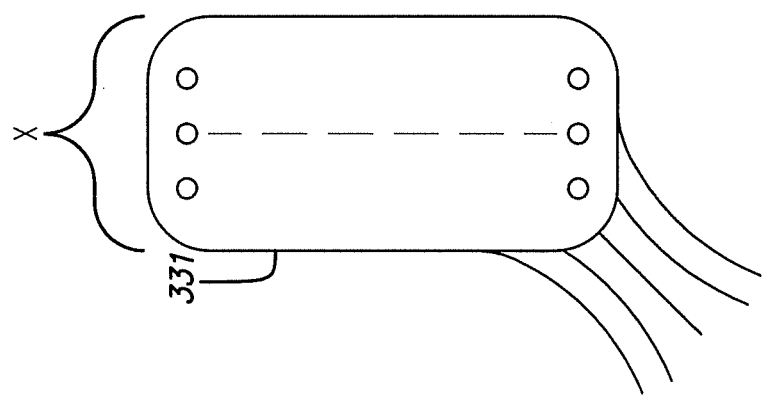
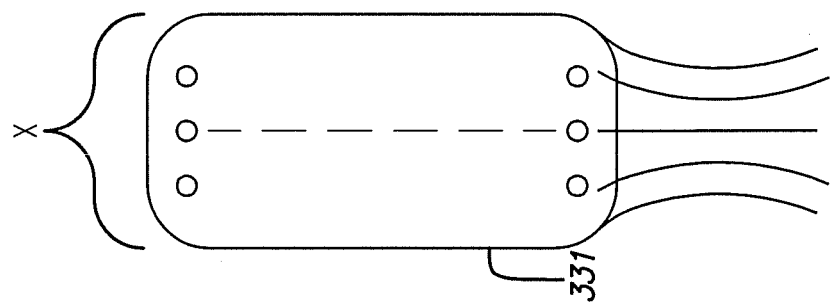

CORTICAL VISUAL PROSTHESIS

CROSS REFERENCE TO RELATED APPLICATIONS

This application claims priority to U.S. Provisional Application 61/760,583, filed Feb. 4, 2013, for Cortical Visual Prosthesis. This application is related to and incorporates by reference U.S. patent application Ser. No. 12/180,436, filed Jul. 25, 2008, for Implantable Device for the Brain; U.S. patent application Ser. No. 11/207,644, for Flexible Circuit Electrode Array; U.S. patent application Ser. No. 11/702,735, for Flexible Circuit Electrode Array; and U.S. Pat. No. 6,974,533, for Platinum Electrode and Method for Manufacturing the Same.

FIELD OF THE INVENTION

The present invention is an implantable device for interfacing with neural tissue of the visual cortex primarily in order to stimulate the neural tissue and create the perception of light in blind individuals.

BACKGROUND OF THE INVENTION

Neural tissue can be artificially stimulated and activated by prosthetic devices that pass pulses of electrical current through electrodes on such a device. The passage of current causes changes in electrical potentials across neuronal membranes, which can initiate neuron action potentials, which are the means of information transfer in the nervous system.

Based on this mechanism, it is possible to input information into the central nervous system by coding the sensory information as a sequence of electrical pulses which are relayed to the central nervous system via the prosthetic device. In this way, it is possible to provide artificial sensations including vision.

More than 1 million people over 40 in the U.S. are legally blind. The economic impact of blindness in this country comes to approximately $51.4 billion, of which about 40% is direct costs. Each year more than 2.5 million eye injuries occur in the U.S. and 50,000 people permanently lose part or all of their vision due to trauma.

Many leading causes of blindness are currently incurable—and once the damage is done, patients with vision loss from diabetic retinopathy, glaucoma, or trauma to the eyes or optic nerve currently have no hope of recovering vision. Treatment options for most types of age-related macular degeneration (AMD), the leading cause of vision loss in older Americans, are limited. Anti-vascular endothelial growth factor (anti-VEGF) drugs may help slow or stop disease progression of wet AMD, and in some cases reverse some vision loss. But patients with severe vision loss from AMD are often without hope of any vision recovery.

Recently, retinal prostheses have become an option for people with diseases resulting in retinal degeneration. The Argus® II Retinal Prosthesis System developed by Second Sight Medical Products, for example, restores partial vision to patients with severe to profound Retinitis Pigmentosa (RP), a relatively rare disease (affecting an estimated 1 in 3037 Americans) that destroys the photoreceptors in the eye. The Argus II is the only treatment available for patients with advanced RP. However, it can only treat patients with damage to the photoreceptors of the retina—the rest of the optic pathway must be intact. To be useful for patients with damage to other parts of the eye and/or optic nerve, a visual prosthesis must directly stimulate neurons downstream in the visual cortex.

A cortical visual prosthesis would offer hope for an estimated 93% of all types of blindness. The concept of cortically based artificial vision had its origins in studies of the functional architecture of the cortex. Penfield and Rasmussen (1950) and Brindley & Lewin (1968) observed that electrical stimulation of the surface of the human visual cortex generally evoked the perception of points of light (phosphenes) at specific regions in space. This forms the principle of operation of a cortical visual prosthesis.

Subsequently, different groups have pioneered work on chronic cortical visual prostheses. To date there have been two categories of cortical implants: penetrating and nonpenetrating (subdural surface stimulation).

Penetrating Electrode Stimulation

The first studies with intracortical implants were performed at the National Institutes of Health (Schmidt et al., 1996) in which penetrating microelectrodes were inserted 1-2 mm into layer 4C of the human visual cortex where the axons from the lateral geniculate nucleus (LGN) terminate in the visual cortex. Acute electric stimulation through these penetrating electrodes elicited phosphenes that were "pin-point to nickel at arm's length" (Schmidt et al., 1996), similar to the phosphenes generated by surface electrodes as discussed below. The threshold for phosphene generation was generally below 5 nC/phase at 200 Hz. Similar thresholds for percept generation were found in other experiments that used microelectrode arrays for chronic cortical stimulation in macaque. These experiments only lasted 2-3 months, likely because the effectiveness of microelectrode stimulation degraded due to scar tissue formation and electrode degeneration. A recent study with an array up to two years after implant reveals a significant increase in response threshold for electrode stimulation, and groups of four or more electrodes are needed to elicit a response after two years.

While providing lower thresholds for shorter term experiments, the lack of long-term stability of penetrating microelectrodes for stimulation likely makes them unsuitable for use in an implant for humans. Their more invasive design also increases the risk of adverse events compared with surface stimulation. Subdural surface cortical stimulation.

The earliest experiments with visual cortical prostheses were performed by Brindley and Dobelle in the 60's and 70's. They stimulated the visual cortex by placing arrays of electrodes on its surface. These experiments provided useful reproducible vision using patterns of around 60 electrodes. In this system, the visual scene was captured by a camera and translated into stimulation patterns that activated neurons in the primary visual cortex. Functional vision corresponding to visual acuities up to 20/1200 (1.8 log MAR) was reported. Two subjects were reported to have a prototype of a functional prosthesis implanted for more than 20 years without infections or other medical problems.

The sizes of the generated phosphenes were fairly independent of the electrode size, and ranged from "a star in the sky" to "a coin at arm's length". The threshold for generation of phosphenes is (anecdotally) reported as 200-1000 nC/phase with 50 Hz stimulation. This is ~50-260 times higher than the mean reported for short term intracortical stimulation in human, but only ~1.2-6.1 times higher than thresholds measured in long term stimulation in macaque.

W. H. Dobelle passed away in 2004. Although we do not condone the lack of U.S. regulatory oversight of Dobelle's experiments in humans, they did demonstrate the feasibility of surface electrode stimulation for long term visual cortical prostheses.

Taken together, these experiments have shown conclusively that electrical stimulation of the visual cortex produces visual perceptions (phosphenes), providing proof-of-concept that an electrode array chronically implanted in the visual cortex could be useful for restoring some vision to blind patients.

Other Visual Prostheses

Since the time of Dobelle's initial work in the early 1970s, the neural implant field has progressed significantly. Several types of neural implants, such as cochlear implants, have been available to patients for decades and are used by hundreds thousands of patients worldwide. Multiple groups are investigating visual prostheses at various places in the visual pathway, such as the optic nerve and the lateral geniculate nucleus (LGN), the two structures of the visual system closest to the eye. Because of these brain structures' relative inaccessibility and compact structure, however, achieving useful vision from such prostheses is difficult.

The greatest progress toward artificial vision to date has been in the development of retinal implants. Retinal prostheses, both epiretinal and subretinal are currently in clinical trials and have been shown to partially restore visual function to patients blinded by retinal degenerative diseases.

Specifically, the Argus II Retinal Prosthesis System is a commercially approved (CE and FDA) neural-interface system that has successfully demonstrated the ability to safely restore partial vision to patients suffering from retinal degenerative diseases such as Retinitis Pigmentosa (RP).

The Argus II Retinal Prosthesis System

The Argus II Retinal Prosthesis System consists of implanted and external components. The implant is an epiretinal prosthesis that includes a receiver, electronics, and an electrode array that are surgically implanted in and around the eye. The array has 60 electrodes arranged in a rectangular grid. The electrodes are made from a proprietary material called "Platinum Grey," which is capable of chronically sustaining charge injection of greater than 1 mC/cm$^2$ in vivo. The electrode array is attached to the retina over the macula with a retinal tack. The external equipment includes glasses, a video processing unit (VPU) and a cable. The glasses include a miniature video camera, which captures video images, and a coil that transmits data and stimulation commands to the implant. The VPU converts the video images into stimulation commands and is body-worn. A cable connects the glasses to the VPU. The Argus II System operates by converting video images into electrical energy that activates retinal cells, delivering the signal through the optic nerve to the brain where it is perceived as light.

The Argus II System is being studied in a clinical trial of 30 subjects in the U.S. and Europe, which began in 2007 and is still ongoing. Results from the clinical trial indicated that the System had an acceptable safety profile: there were no unexpected adverse events, and all (expected) adverse events that did occur were successfully treated with standard ophthalmic techniques. The implanted System showed good stability, with only one device failure (due to damage of the device during surgery) as of December 2012—over 120 subject-years. All Systems created visual percepts, and all subjects used the device at home. Overall, the System improved subjects' ability to perform visual function tasks (finding a high-contrast object, determining the direction of motion of an object) and functional vision tasks (real-world orientation and mobility).

SUMMARY OF THE INVENTION

The present invention is a visual prosthesis adapted for implantation in the brain, and more particularly with an electrode array adapted for implantation in the Calcarine Sulcus of the visual cortex. The electrode array of the invention has electrodes on each side and spaced appropriately for the Calcarine Sulcus and driven by an electronic circuit within a hermetic package small enough to be implanted with a skull.

BRIEF DESCRIPTION OF THE DRAWINGS

FIGS. 5A-C show alternate cable angles approach angles for the electrode array.

In the following description, like reference numbers are used to identify like elements. Furthermore, the drawings are intended to illustrate major features of exemplary embodiments in a diagrammatic manner. The drawings are not intended to depict every feature of every implementation nor relative dimensions of the depicted elements, and are not drawn to scale.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1A:
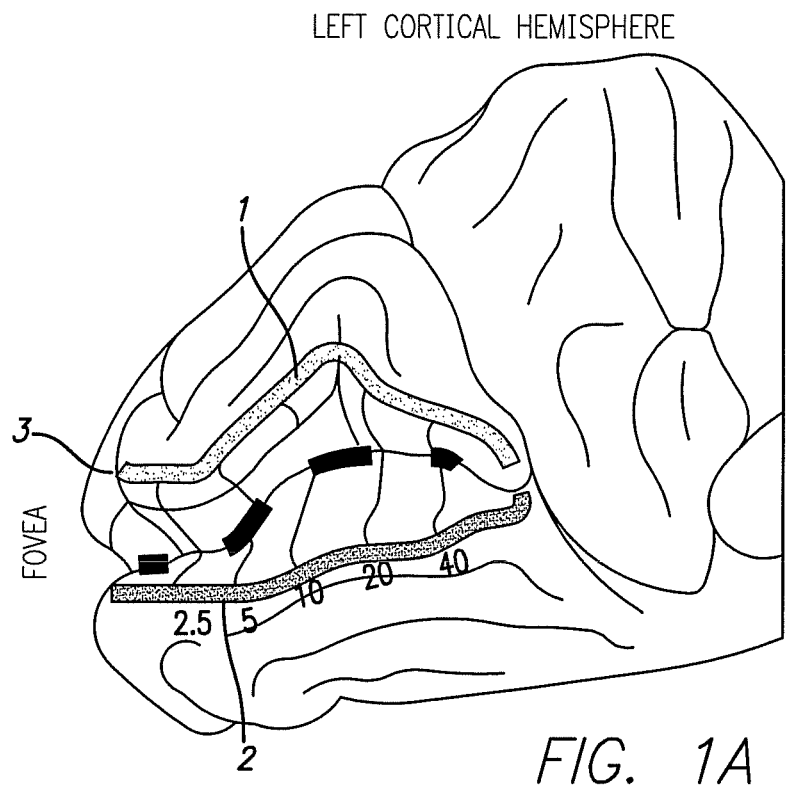
FIGS. 1A-E shows the Calcarine Sulcus where to electrode array of the preferred visual prosthesis is to be implanted.
Figure 1B:
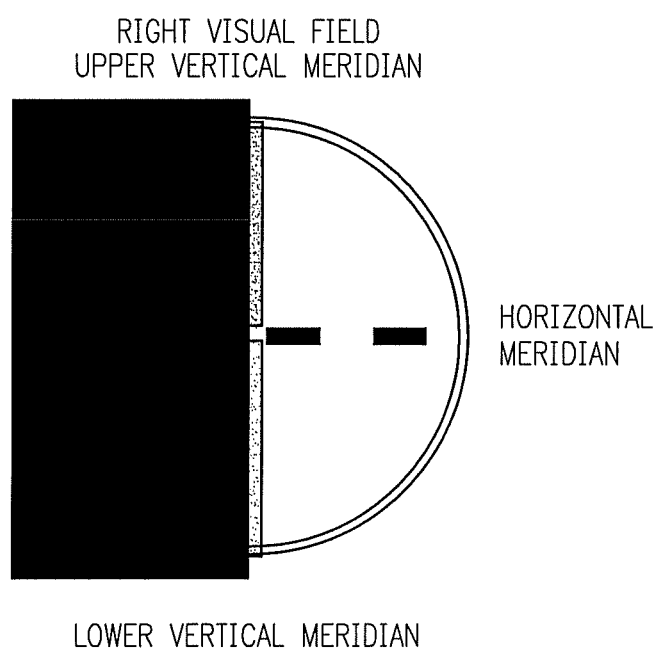
Figure 1C:
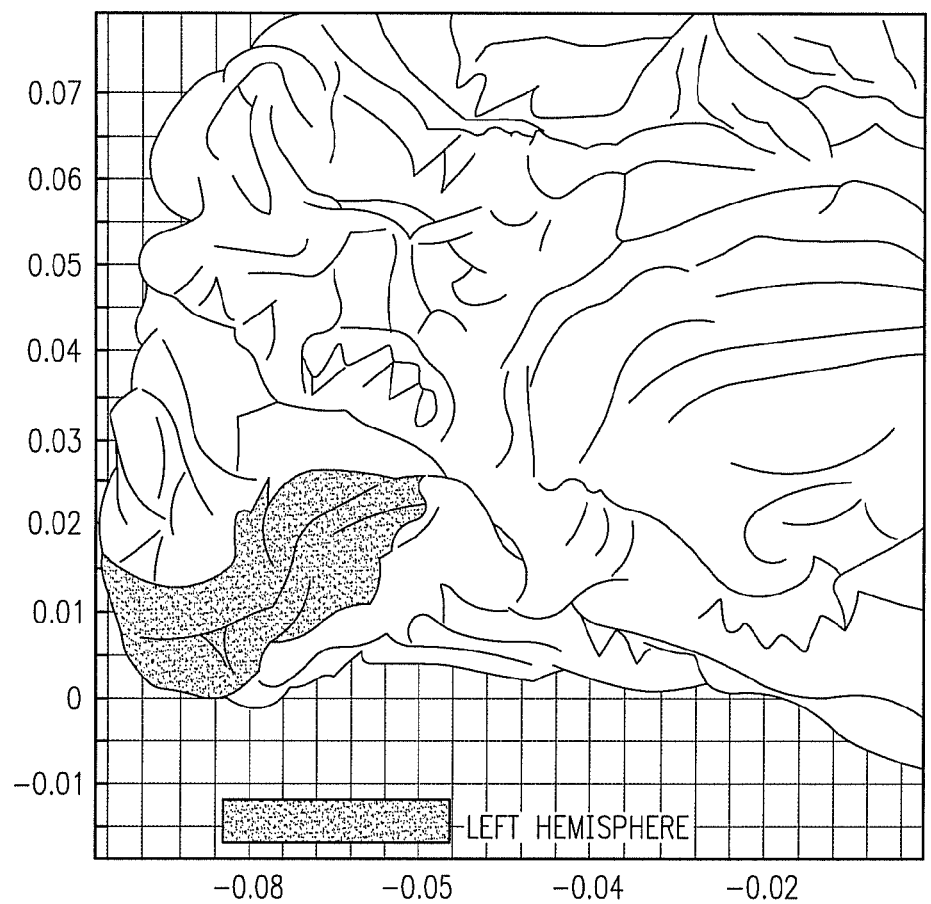
Figure 1D:
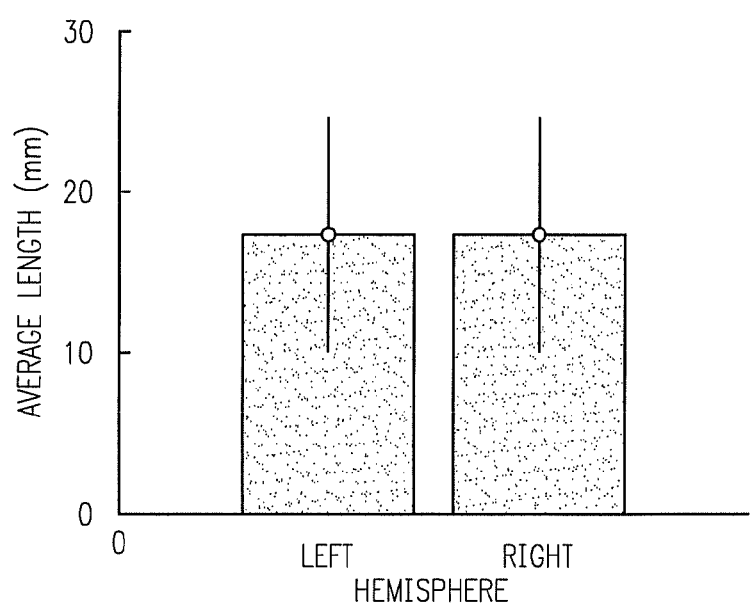
Figure 1E:
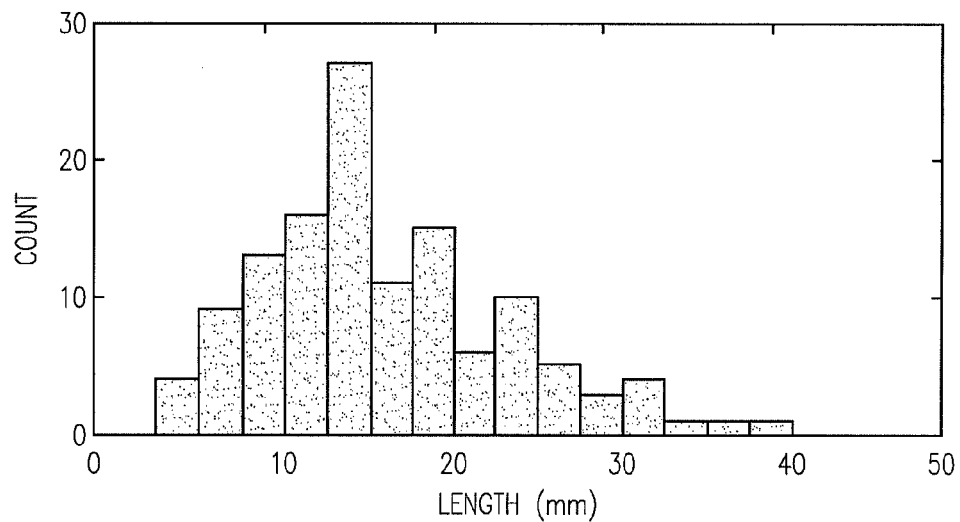

FIG. 1A, shows the left side of the back of a human brain as seen from the medial longitudinal fissure. It is opened up for visibility. The fovea 4 in the back of the head maps out the central visual field. Mappings of the Lower vertical meridian 1, Upper vertical meridian 2 and Horizontal meridian 3 (dashed), of the right visual field shown in FIG. 1B. FIG. 1C is an example of V1 in left hemisphere of a subject. FIG. 1D is the average length of the left and right calcarine sulcus for 63 subjects. FIG. 1E is a Histogram of the number of length measurements for all subjects left and right.

Figure 2:
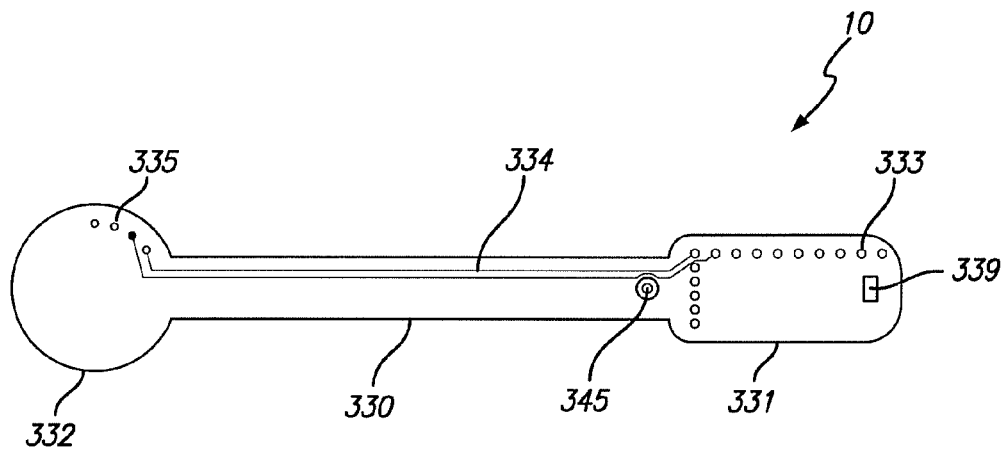
FIG. 2 shows the thin film array of the present invention.

Referring to FIG. 2, a polymer-based flexible circuit includes a cable portion 330, an electrode array portion 331, and a bond pad portion 332. The bond pad portion 332 is attached to the electronics package shown in FIG. 9. The cable portion 330, bond pad portion 332, and array portion 331 are formed from a single integrated flexible circuit 10 with bond pads 335, suitable to connect to the electronics package in the bond pad portion 332 at the proximal end and electrodes 333 in the array portion 331 at the distal end. The flex circuit 10 is composed of a base polymer layer, at least one interlayer of patterned metal (or a stack up of metals)

comprising bond pads 335, traces 334, and electrodes 333, and covered by a top polymer layer. The bottom and top polymer layers are patterned to expose the pads and/or electrodes, but insulate the traces. Such a flexible circuit 10 and may be manufactured in a manner disclosed in patent application Ser. Nos. 11/207,644, 11/702,735 incorporated herein by reference. The flexible circuit 10 may consist of more than one metal interlayer and corresponding additional polymer interlayers so that the thin film flexible circuit 10 may be considered a multilayer structure. In a more preferable embodiment, the polymer employed for the base layer, inter layer(s), and top layer is polyimide. Other possible polymers include parylene, silicone, Teflon, PDMS, PMMA, PEG, and others.

An electrode array portion 331 will between 2 to 6 mm by 10 to 20 mm, and preferably be about 4 by 15 mm, with some electrodes placed outside the calcarine sulcus on the V1 gyrus. There will be preferably at least 30 stimulating electrodes on each side. The electrodes 333 will be about 500 µm in diameter, arranged in a 3 by 10 pattern on each side, with about 1000 µm between columns and about 1250 µm between rows to maximize distribution as well as allowing for traces routing to all electrodes. Sixty stimulating electrodes of that size can be supported by the known electronics of the Argus II array. As with the Argus II, human functional studies will ultimately be required to determine the optimal contact size and spacing, including considerations of potential impact on cortical magnetization factor (CMF), the receptive field sizes (RF), and impedance. It has been shown that the population point image (PPI=RF×CMF) is nearly constant with eccentricity in V1 (Harvey and Dumoulin, 2011), and the pool of neurons activated by electric stimulation is largely unaffected by electrode sizes (Histed et al., 2009).

The electrode array will be fabricated from polyimide dielectric films encapsulating platinum conductive traces. Openings in the polyimide will be electroplated with platinum grey as described in U.S. Pat. No. 6,974,533, which is corporate herein by reference, to form electrodes as we have done previously. This material set has demonstrated excellent reliability in chronically implanted neurostimulator devices with stimulation at charge densities exceeding 1 $mC/cm^2$, and thus can safely deliver over 1964 nC/phase for a 500 µm disk electrode. Advanced multilayer construction techniques will provide flexibility in the electrode grid placement. We have demonstrated initial feasibility of creating electrodes on both sides of the polyimide electrode array, which minimizes thickness and eliminates any folding—both of which improve the flexibility of an electrode array and will improve conformance to the cortical tissue.

Since an array in the calcarine sulcus will be held in place by the cortical surface on both sides, minimal sutures or other efforts to hold it in place will be needed. Alternatively, anchors may be added to the array design to attach it to the pia with microsutures. Because the pia/arachnoid and the dura/skull move with respect to each other, it is critical that the sutures not connect the embedded electrode to the dura or skull, as any movement of the electrode in the calcarine sulcus may cause the edge of the electrode array to damage surrounding tissue. The design of the novel flexible electrode array may incorporate an elongated, integrated, flexible s-shaped polyimide cable, reinforced with at least one Dacron sheet to accommodate movement of the brain relative to the dura and skull; this is inspired by the commonly used strain-relief loop used in current neurosurgical procedures. To avoid damage to tissue from sharp array edges, the array will be given a silicone bumper, as is the case with our current electrode array for the Argus II Retinal Prosthesis System.

Many of the other components of the Argus II will be directly applicable to the new cortical prosthesis. The external system—glasses, transmitter coil and VPU—can be used in the cortical system with very few changes other than the relocation of the external coil from the glasses to the back of the head. An implanted magnet could aid positioning as in some cochlear implants. The implant's internal electronics is also adequate for use in a cortical prosthesis. The current Argus II internal coil and electronics drive a 60-electrode array. A close review of the visual cortical prosthesis literature suggests that the current amplitudes required to generate phosphenes with surface electrodes and biphasic stimulation is 200-1000 nC/phase in humans. Similar thresholds are reported with surface stimulation in primates in behavioral experiments. Further experiments in motor cortex indicate that surface stimulation in Calcarine Sulcus requires only about 25% the charge of gyral stimulation for perceptual threshold, likely because of better apposition between the electrodes and the target neurons. Therefore it is likely that the charge required to produce visual perception will be much less in this array design than that found by Dobelle et al. (1976) for surface electrode arrays. The Argus II electronics can yield amplitudes up to ~4000 nC/phase. Thus, the current electronics are capable of delivering a total charge of ~4-20 times the thresholds reported for generating phosphenes in humans.

Figure 3A:
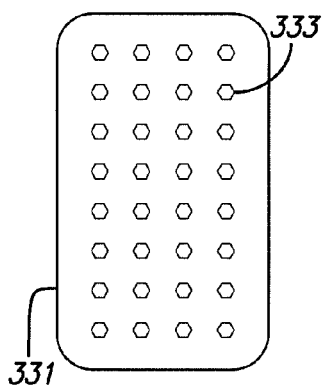
FIGS. 3A-C show the preferred arrangement of electrodes on the electrode array.
Figure 3B:
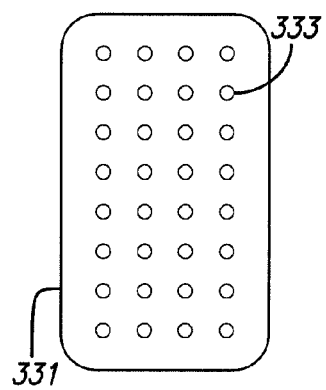
Figure 3C:
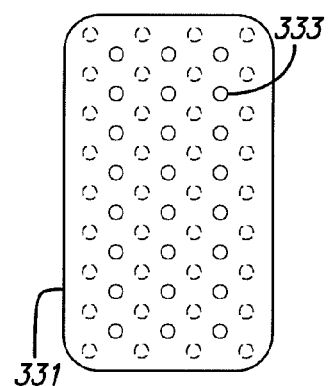
Figure 4A:
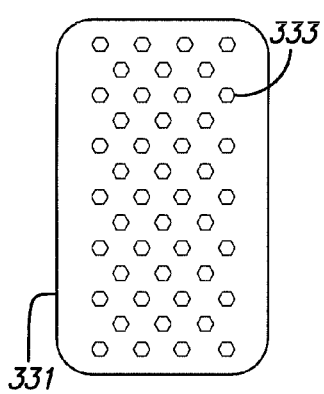
FIGS. 4A-C show alternate arrangement of electrodes on the electrode array.
Figure 4B:
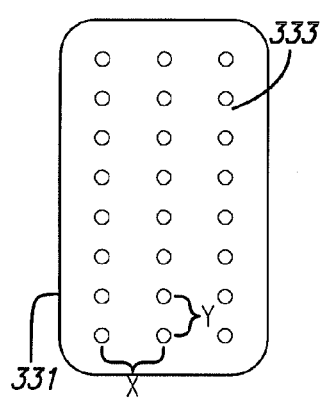

Arrays to fit in the Calcarine Sulcus will have electrodes on both sides. This way they can stimulate both the upper and lower part of the visual field. The electrodes on each side can be either on top of each other or aligned with each other (FIG. 3A+B) or not overlapping or offset from each other (FIG. 3A+C). Further, the electrode pattern can be of different designs. For example square (FIG. 3), hexagonal (FIG. 4A), rectangular with a different distance, x and y, between rows and columns (FIG. 4B).

Figure 4C:
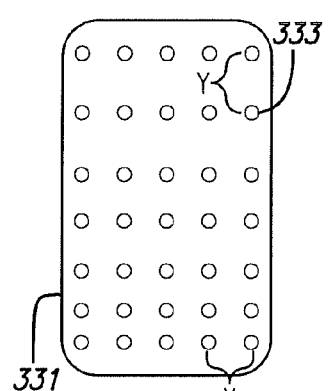

The cortical magnification factor varies in visual cortex, with a bigger part of cortex devoted to foveal than peripheral visual processing, i.e. the amount of cortex devoted to representing a unit of vision (say 1 degree of visual angle) is highest in the fovea and declines with the visual angle away from the fovea. Following this, the electrodes can be arranged with a varying density or pitch as illustrated in FIG. 4C, with higher electrode density closer to the fovea. It is a given that more electrodes and higher densities can only be of benefit, but it will depend on the connecting electronics and the ability to make higher electrode densities. The current Argus II system has 60 electrodes, so using this we could plan for 25-30 electrodes on each side of an array. But we can also go higher in the future.

From the discussion related to FIG. 1, we saw that the depth of the sulcus is 5-9 mm. The length of the Calcarine Sulcus spanning V1 ranges from 4 to 40 mm with a mean of 17.3 mm.

The width of the array (x in FIG. 5) should be smaller than or equal to the depth of the sulcus to fit entirely inside the sulcus, so smaller than 5-9 mm. Ideally we would want it as wide as possible, so min 4-5 mm and max 5-9 mm.

The length of the array should be 4-40 mm. It does not matter if the array is longer than the V1 part of the Calcarine Sulcus, but it doesn't help either. Based on FIG. 1D it is recommended that the length be between 10 to 20 mm, which would fit in all Calcarine Sulci and provide decent visual field coverage. Since the anterior end of the Calcarine Sulcus represent the visual fovea, the longer the array, the larger the visual field. But a few cm covers ~20+ degrees of visual angle for most people.

Figure 6:
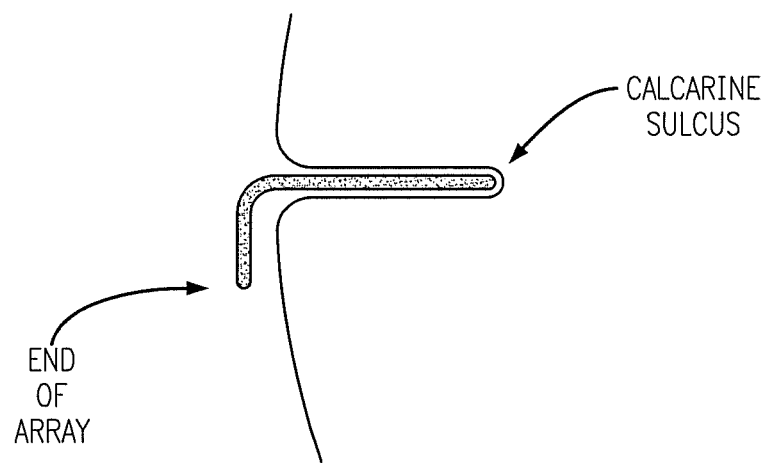
FIG. 6 shows the electrode array within the Calcarine Sulcus.
Figure 7:
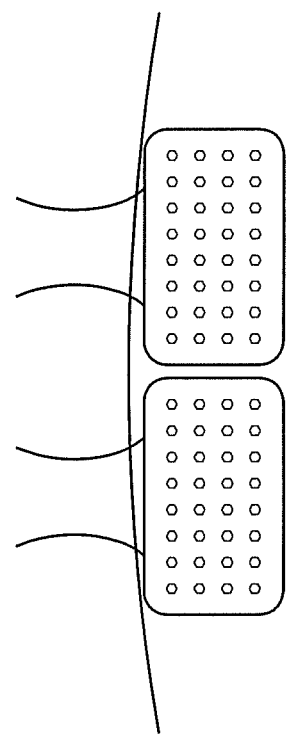
FIG. 7 shows an alternate embodiment with two electrode arrays within the Calcarine Sulcus.

The connection to the electronics, for example of Argus II style, can be either from one side or the corner (FIG. 5) of the array. If the connection is from one side, that side can stick out of the Calcarine Sulcus and be bent to the surface of cortex (FIG. 6). This could be used to cover part of V1 not in the Calcarine Sulcus. Specifically for FIG. 5C, this would allow the width of the array to be larger than the 5-9 mm which is the depth of the Calcarine Sulcus. If the arrays are smaller, more arrays can be placed side-by-side in the Calcarine sulcus (FIG. 7).

It is important for the array to be made of flexible material so it is bendable. This is both for eventual parts of the array sticking out of the Calcarine Sulcus and for the part inside the Calcarine Sulcus. For example in FIG. 1A, shows an example where the Calcarine Sulcus has an "s" shape.

Further it is recommended that the array has a bumper to avoid sharp edges, which could damage the neural tissue.

Experiments have shown that the current needed from surface electrodes to stimulate cortical neurons and yield phosphenes is on the order of mA. So the electrodes should be able to provide this level of current.

Ohm's law (U=IR) constrains the electrode size for this desired current. Of course the electrodes can be infinitely small (large R) if the charge (U) is large enough. But high charges can damage the neural tissue and would require strong batteries/electronics.

The electrodes in Argus II are ~100 µm in diameter and can the system can deliver 1 mA capped by software and the electronics can deliver a bit more. This is around what is needed. With the current Argus II electrode coating material and electronics it suggests the electrode diameters need to be in the same range as the Argus II electrodes. Say 50-1000 µm in diameter, if round but other shapes e. g. oval or rectangular are possible.

Figure 8:
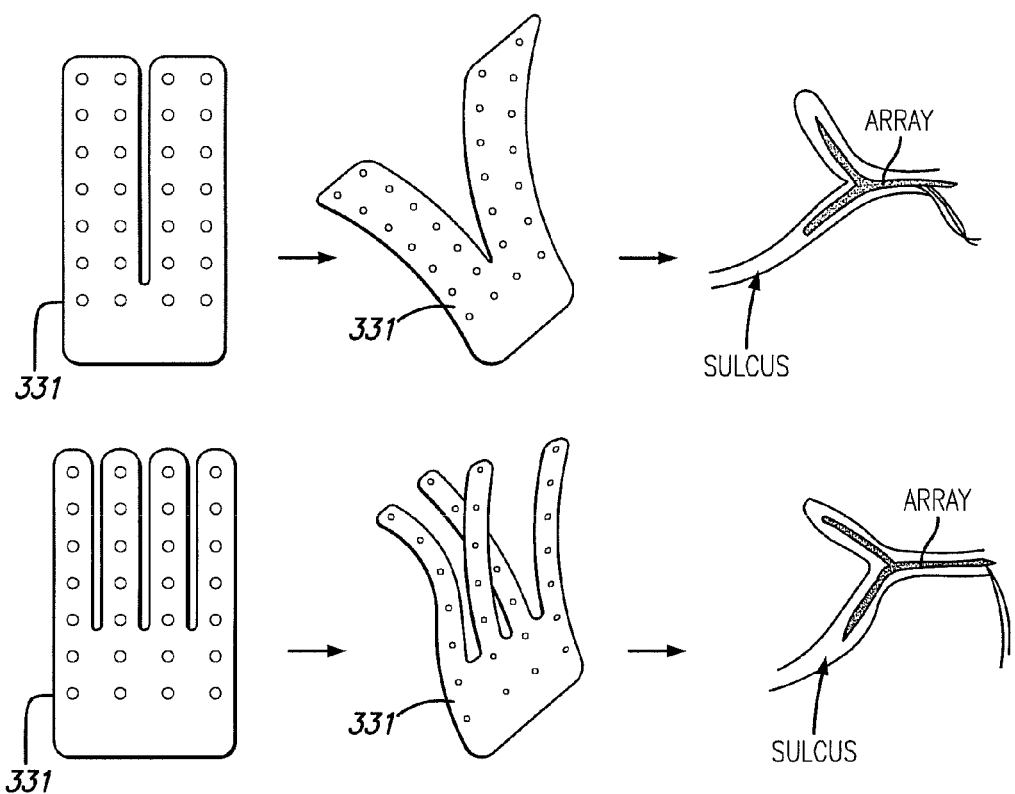
FIG. 8 shows an alternate electrode array with branched segments for a branched Calcarine Sulcus.

The two images on FIG. 1 shows an unbranched Calcarine Sulcus and a Calcarine Sulcus with a branch. From the data provided by Justin Ales, we observed such branching in ~10% of the Calcarine Sulci. One way to cover the cortical surface in branching Calcarine Sulci would be to put a smaller array in the branch, similar to FIG. 7. Another way could be to design the array with forks so some can go in each branch as illustrated in FIG. 8.

Figure 9:
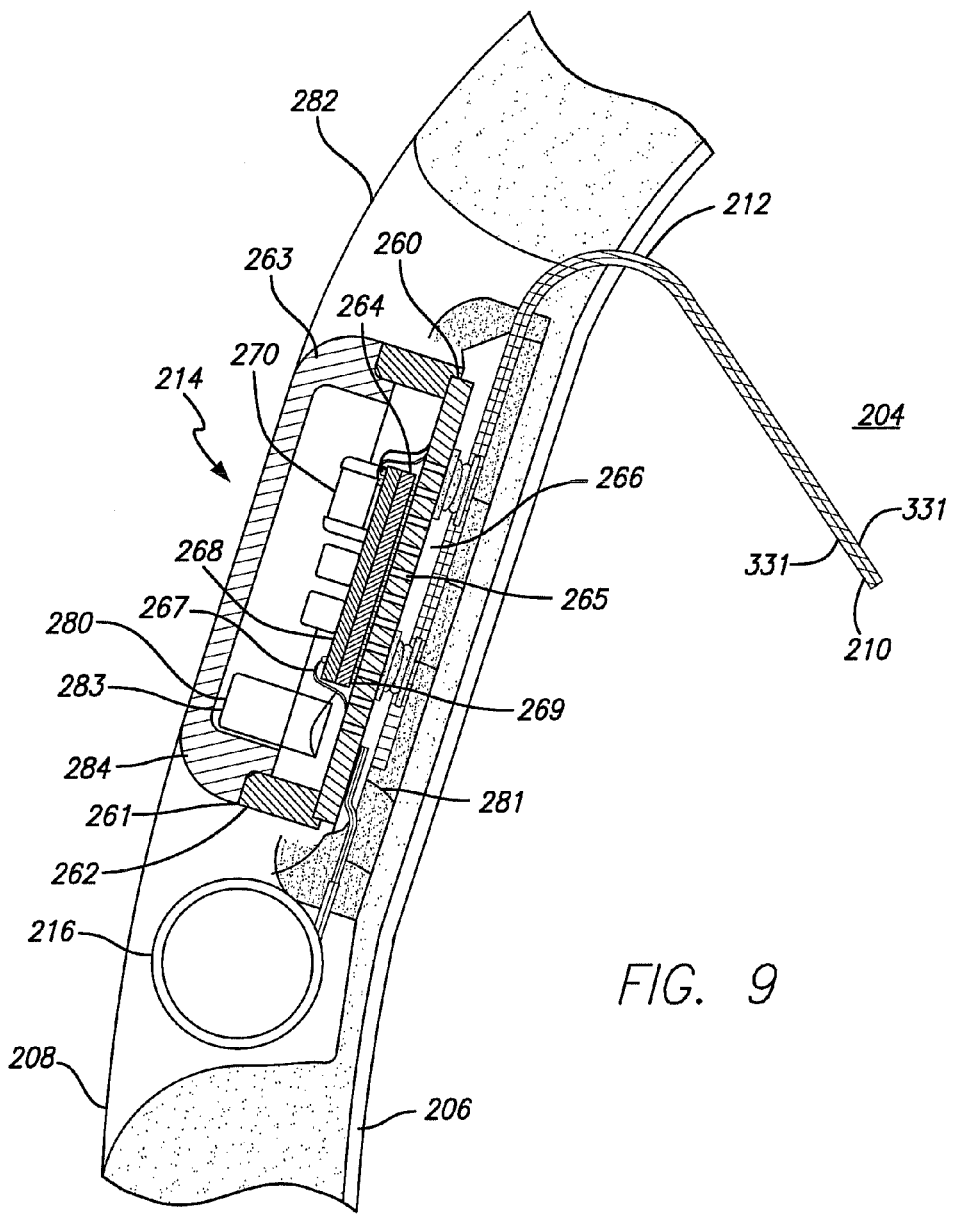
FIG. 9 the preferred implantation of the driver circuitry according to the preferred embodiment.

Another necessary change is the placement of the internal coil and electronics case; rather than placing them under the conjunctiva (fixed with a scleral band) as in the Argus II, the electronics for the cortical prosthesis will be affixed to the skull (FIG. 9). This is similar to the placement used for the Neuropace closed loop stimulator for epilepsy, and the first generation of the Argus implant and should not pose any significant engineering challenges.

FIG. 9 shows application of the package of the present invention to visual cortex stimulation. Due to the low profile of the package, the package 214 can be implanted in a hollowed out portion of the cranium 208. The hollowed out portion may go part way through the cranium 208, leaving part of the bone under the package 214. Alternatively, the hollowed out portion may extend through the cranium and the package 214 rests on the durra 206. This protects the package 214, allows the package 214 to be placed close to the stimulation site, and avoids visible protrusions on the head. The package 214 contains a ceramic substrate 260, with metallized vias 265 and thin-film metallization 266. The package 214 contains a metal case wall 262 which is connected to the ceramic substrate 260 by braze joint 261. On the ceramic substrate 260 an underfill 269 is applied. On the underfill 269 an integrated circuit chip 264 is positioned. On the integrated circuit chip 264 a ceramic hybrid substrate 268 is positioned. On the ceramic hybrid substrate 268 passives 270 are placed. Wirebonds 267 are leading from the ceramic substrate 260 to the ceramic hybrid substrate 268. A metal lid 284 is connected to the metal case wall 262 by laser welded joint 263 whereby the package 214 is sealed. A thin film array cable 212 leads to an electrode array 210 for stimulation of the visual cortex 204. A coil 216 is placed close to the scalp to receive inductive power and data from an external coil (not shown).

Also, a cover 282 such as Dacron mesh may be used to hold the package 216 in place. The cover 282 may be glued or screwed to the cranium. It should be noted that the package 214 is placed with the delicate ceramic substrate 260 protected with the more durable metal lid 284 just beneath the scalp.

Accordingly, what has been shown is an improved method making a hermetic package for implantation in a body. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What we claim is:

1. A visual prosthesis comprising:
   a flexible circuit and including a bond pad portion, and cable portion and an electrode array portion including stimulating electrodes including a platinum grey surface coating on a first side of the flexible circuit and stimulating electrodes including a platinum grey surface coating on a second side opposite the first side, offset from the electrodes on the first side and, adapted to stimulate neurons in the brain;
   a driver circuit driving stimulation signals on the flexible circuit, the driver circuit within a hermetic housing suitable to be implanted with a head; and
   a coil providing power and data to the driver circuit.

2. The visual prosthesis according to claim 1, wherein flexible circuit includes more than one branch suitable to stimulate different regions.

3. The visual prosthesis according to claim 2, wherein the flexible circuit includes four or more branches.

4. The visual prosthesis according to claim 1, wherein the electrodes are organized on the flexible circuit in a rectangular pattern.

5. The visual prosthesis according to claim 1, wherein the electrodes are organized on the flexible circuit in a hexagonal pattern.

6. The visual prosthesis according to claim 1, wherein the electrodes are organized in the flexible circuit having varying pitch.

7. The visual prosthesis according to claim 6, wherein the varying pitch is closer toward the fovea of the Calcarine Sulcus.

8. The visual prosthesis according to claim 1, wherein the electrode array portion is between 2 to 6 mm by 10 to 20 mm.

9. The visual prosthesis according to claim 1, wherein the electrode array portion is about 4 by 15 mm.

10. The visual prosthesis according to claim 1, wherein the flexible circuit is constructed of polyimide dielectric films encapsulating platinum conductive traces.

11. The visual prosthesis according to claim 1, wherein the flexible circuit includes soft polymer bumpers around at least a portion of its edges.

12. The visual prosthesis according to claim 11, wherein the soft polymer is silicone.

13. The visual prosthesis according to claim 1, wherein the driver circuit or coil includes a magnet suitable to locate an external coil in proper relation to the coil.

14. The visual prosthesis according to claim 1, wherein the electrodes are arranged in a pattern with a width length greater than a width and the cable portion attaching to the electrode array portion at its length.

15. The visual prosthesis according to claim 1, wherein the electrodes are arranged in a pattern with a width length greater than a width and the cable portion attaching to the electrode array portion at its width.

16. The visual prosthesis according to claim 1, wherein the electrodes are arranged in a pattern with a width length greater than a width and the cable portion attaching to the electrode array portion at a corner between its length and width.

* * * * *